(12) United States Patent
Stahmann et al.

(10) Patent No.: US 8,612,000 B2
(45) Date of Patent: Dec. 17, 2013

(54) LEFT VENTRICULAR PACING PROTECTION IN THE CONTEXT OF MULTI-SITE LEFT VENTRICULAR PACING

(75) Inventors: Jeffrey E. Stahmann, Ramsey, MN (US); James O. Gilkerson, Stillwater, MN (US); Krzysztof Z. Siejko, Maple Grove, MN (US); Yinghong Yu, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 13/327,414

(22) Filed: Dec. 15, 2011

(65) Prior Publication Data

US 2012/0158083 A1    Jun. 21, 2012

Related U.S. Application Data

(60) Provisional application No. 61/424,953, filed on Dec. 20, 2010.

(51) Int. Cl.
- *A61N 1/368* (2006.01)
- *A61N 1/362* (2006.01)
- *A61N 1/36* (2006.01)
- *A61N 1/365* (2006.01)

(52) U.S. Cl.
USPC .................................. 607/9; 607/17; 607/25

(58) Field of Classification Search
USPC .......................................................... 607/17
See application file for complete search history.

(56) References Cited

U.S. PATENT DOCUMENTS

| | | |
|---|---|---|
| 6,438,421 B1 | 8/2002 | Stahmann et al. |
| 6,480,740 B2 | 11/2002 | Stahmann et al. |
| 6,496,730 B1 | 12/2002 | Kleckner et al. |
| 6,512,952 B2 | 1/2003 | Stahmann et al. |
| 6,553,258 B2 | 4/2003 | Stahmann et al. |
| 6,574,506 B2 | 6/2003 | Kramer et al. |
| 6,795,734 B2 * | 9/2004 | Vanderlinde et al. ........... 607/27 |
| 6,829,505 B2 | 12/2004 | Kramer et al. |
| 6,871,095 B2 | 3/2005 | Stahmann et al. |

(Continued)

FOREIGN PATENT DOCUMENTS

| | | |
|---|---|---|
| WO | WO-0113995 A1 | 3/2001 |
| WO | WO-0136043 A1 | 5/2001 |
| WO | WO-2010054359 A2 | 5/2010 |
| WO | WO-2012087758 A3 | 6/2012 |

OTHER PUBLICATIONS

Neuzner, J., et al., "Biventricular triggered pacing increases contractile function in heart failure patients with atrial fibrillation and prolonged QRS duration", PACE, 24, (2001), 729.

(Continued)

*Primary Examiner* — Carl H Layno
*Assistant Examiner* — Erin Piateski
(74) *Attorney, Agent, or Firm* — Schwegman Lundberg & Woessner, P.A.

(57) ABSTRACT

In a pacing mode where the left ventricle is paced upon expiration of an escape interval that is reset by a right ventricular sense, there is the risk that the left ventricular pace may be delivered in the so-called vulnerable period that occurs after a depolarization and trigger an arrhythmia. To reduce this risk, a left ventricular protective period (LVPP) may be provided. Methods and devices for implementing an LVPP in the context of multi-site left ventricular pacing are described.

10 Claims, 11 Drawing Sheets

(56) References Cited

U.S. PATENT DOCUMENTS

| | | |
|---|---|---|
| 6,963,774 B2 | 11/2005 | Stahmann et al. |
| 7,003,347 B2 | 2/2006 | Stahmann |
| 7,013,176 B2 * | 3/2006 | Ding et al. .................. 607/9 |
| 7,058,449 B2 | 6/2006 | Stahmann et al. |
| 7,130,689 B1 | 10/2006 | Turcott |
| 7,142,914 B2 | 11/2006 | Stahmann et al. |
| 7,191,001 B2 | 3/2007 | Stahmann et al. |
| 7,260,432 B2 | 8/2007 | Kramer et al. |
| 7,379,773 B2 * | 5/2008 | Stahmann et al. ........... 607/9 |
| 7,403,818 B2 | 7/2008 | Kramer et al. |
| 7,440,802 B2 * | 10/2008 | Stahmann et al. ........... 607/9 |
| 7,536,223 B2 | 5/2009 | Stahmann et al. |
| 7,546,160 B2 * | 6/2009 | Stahmann et al. ........... 607/9 |
| 7,630,765 B2 | 12/2009 | Stahmann et al. |
| 2002/0082655 A1 * | 6/2002 | Kramer et al. ............... 607/9 |
| 2002/0082656 A1 | 6/2002 | Stahmann et al. |
| 2002/0082657 A1 * | 6/2002 | Stahmann et al. ........... 607/9 |
| 2003/0028222 A1 | 2/2003 | Stahmann |
| 2003/0130702 A1 | 7/2003 | Kramer et al. |
| 2004/0158293 A1 | 8/2004 | Yonce et al. |
| 2004/0225330 A1 | 11/2004 | Kramer et al. |
| 2005/0165453 A1 | 7/2005 | Stahmann et al. |
| 2005/0216066 A1 | 9/2005 | Auricchio et al. |
| 2006/0004418 A1 | 1/2006 | Stahmann et al. |
| 2006/0206156 A1 * | 9/2006 | Stahmann et al. ........... 607/9 |
| 2007/0016260 A1 * | 1/2007 | Baker et al. ................ 607/14 |
| 2008/0046057 A1 * | 2/2008 | Kramer et al. ............ 607/121 |
| 2008/0097536 A1 * | 4/2008 | Kramer et al. ............... 607/9 |
| 2008/0177344 A1 * | 7/2008 | Maskara et al. ............. 607/25 |
| 2008/0288012 A1 | 11/2008 | Kramer et al. |
| 2009/0043350 A1 * | 2/2009 | Stahmann et al. .......... 607/25 |
| 2010/0049270 A1 | 2/2010 | Pastore et al. |
| 2010/0063560 A1 | 3/2010 | Stahmann et al. |
| 2012/0158084 A1 | 6/2012 | Stahmann et al. |
| 2012/0158085 A1 | 6/2012 | Stahmann et al. |
| 2012/0158087 A1 | 6/2012 | Stahmann et al. |

OTHER PUBLICATIONS

"International Application Serial PCT/US2011/065251, International Search Report mailed May 29, 2012", 5 pgs.

"International Application Serial No. PCT/US2011/065251, Written Opinion mailed May 29, 2012", 7 pgs.

"International Application Serial No. PCT/US2011/065255, Search Report mailed Oct. 17, 2012", 4 pgs.

"International Application Serial No. PCT/US2011/065255, Written Opinion mailed Oct. 17, 2012", 7 pgs.

"International Application Serial No. PCT/US2011/065259, International Search Report mailed Mar. 19, 2012", 5 pgs.

"International Application Serial No. PCT/US2011/065259, Written Opinion mailed Mar. 19, 2012", 7 pgs.

"International Application Serial No. PCT/US2011/065260, International Search Report mailed Apr. 4, 2012", 5 pgs.

"International Application Serial No. PCT/US2011/065260, Written Opinion mailed Apr. 4, 2012", 9 pgs.

* cited by examiner

LEFT VENTRICULAR PACING PROTECTION IN THE CONTEXT OF MULTI-SITE LEFT VENTRICULAR PACING

CLAIM OF PRIORITY

This application claims the benefit of priority under 35 U.S.C. §119(e) of Stahmann et al., U.S. Provisional Patent Application Ser. No. 61/424,953, entitled "LEFT VENTRICULAR PACING PROTECTION IN THE CONTEXT OF MULTI-SITE LEFT VENTRICULAR PACING", filed on Dec. 20, 2010, which is herein incorporated by reference in its entirety.

FIELD OF THE INVENTION

This invention pertains to devices and methods for cardiac rhythm management. In particular, the invention relates to a device and method for delivering cardiac resynchronization therapy.

BACKGROUND

Heart failure (HF) refers to a clinical syndrome in which an abnormality of cardiac function causes a below normal cardiac output that can fall below a level adequate to meet the metabolic demand of peripheral tissues. Heart failure can be due to a variety of etiologies with ischemic heart disease being the most common. Heart failure can be treated with a drug regimen designed to augment cardiac function or by pacing therapy. It has been shown that some heart failure patients suffer from intraventricular and/or interventricular conduction defects (e.g., bundle branch blocks) such that their cardiac outputs can be increased by improving the synchronization of ventricular contractions with electrical stimulation. In order to treat these problems, implantable cardiac devices have been developed that provide appropriately timed electrical stimulation to one or more heart chambers in an attempt to improve the coordination of atrial and/or ventricular contractions, termed cardiac resynchronization therapy (CRT). Ventricular resynchronization is useful in treating heart failure because, although not directly inotropic, resynchronization can result in a more coordinated contraction of the ventricles with improved pumping efficiency and increased cardiac output.

DETAILED DESCRIPTION

Described herein are methods and devices that are specifically applicable to the delivery of cardiac resynchronization therapy using multiple left ventricular sites. Delivering such multi-site left ventricular pacing in an optimum manner requires modifications to certain operational features that have been implemented in existing devices for delivering cardiac resynchronization therapy as single-site left ventricular pacing. As described below, these features relate to the management of refractory periods, the implementation of a left ventricular protective period, providing right ventricular safety pacing in a left ventricle-only pacing mode, and implementation of a biventricular-triggered pacing mode.

Hardware Description

Figure 1:
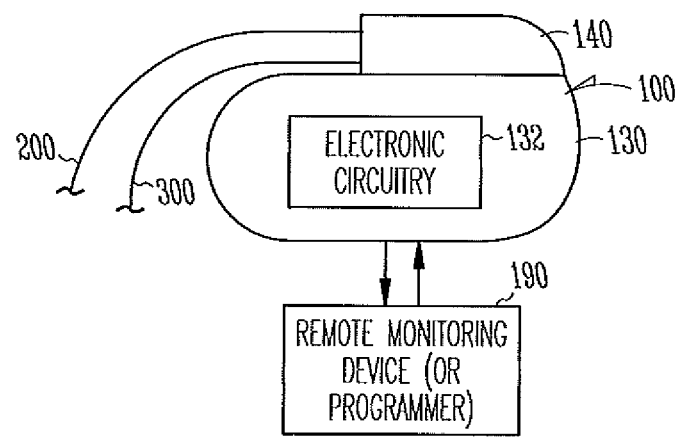
FIG. 1 shows the components of an exemplary device.

Implantable pacing devices are typically placed subcutaneously or submuscularly in a patient's chest with leads threaded intravenously into the heart to connect the device to electrodes disposed within a heart chamber that are used for sensing and/or pacing of the chamber. A programmable electronic controller causes the pacing pulses to be output in response to lapsed time intervals and/or sensed electrical activity (i.e., intrinsic heart beats not as a result of a pacing pulse). FIG. 1 shows the components of an implantable pacing device 100 that includes a hermetically sealed housing 130 that is placed subcutaneously or submuscularly in a patient's chest. The housing 130 may be formed from a conductive metal, such as titanium, and may serve as an electrode for delivering electrical stimulation or sensing in a unipolar configuration. A header 140, which may be formed of an insulating material, is mounted on the housing 130 for receiving leads 200 and 300 which may be then electrically connected to pulse generation circuitry and/or sensing circuitry. Contained within the housing 130 is the electronic circuitry 132 for providing the functionality to the device as described herein which may include a power supply, sensing circuitry, pulse generation circuitry, a programmable electronic controller for controlling the operation of the device, and a telemetry transceiver capable of communicating with an external programmer or a remote monitoring device 190.

Figure 2:
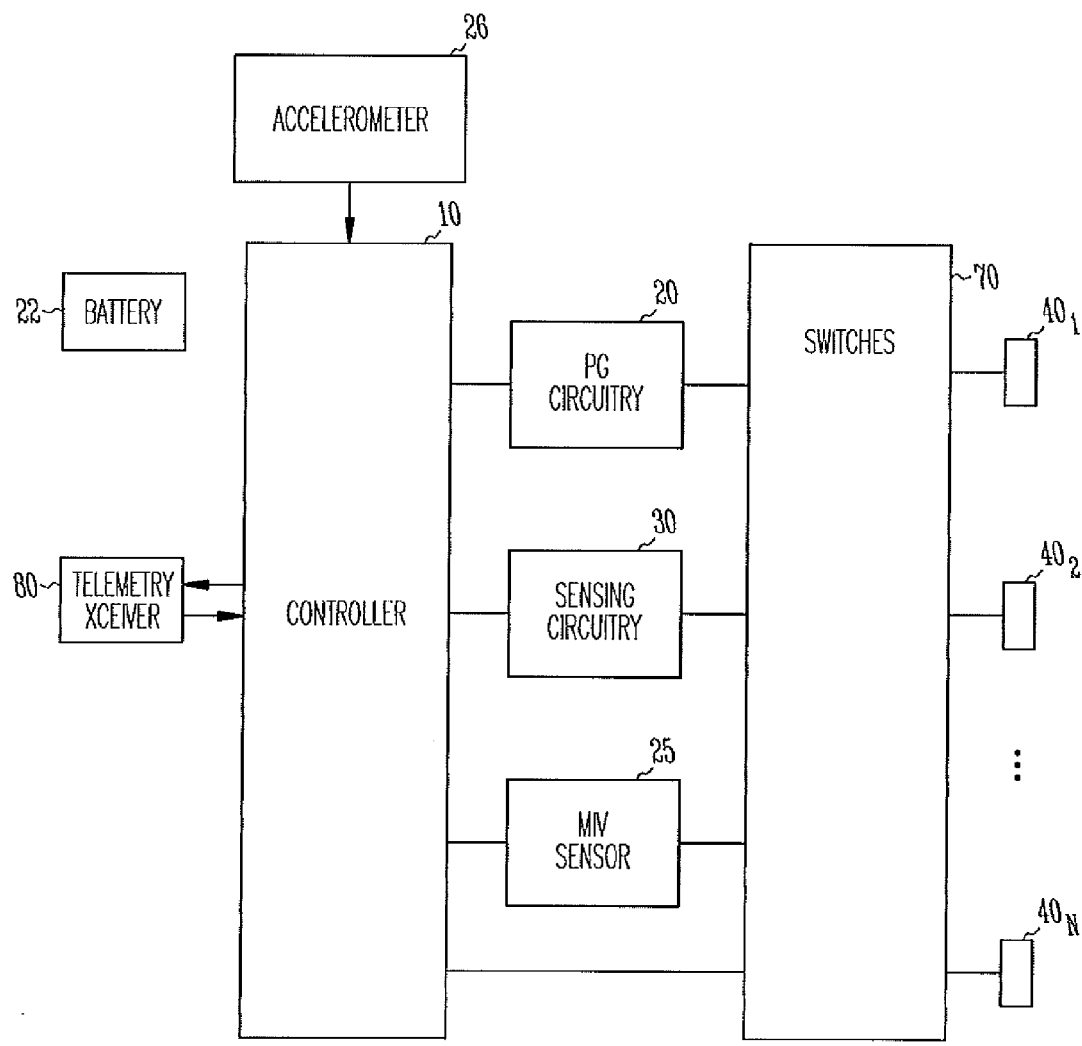
FIG. 2 is a block diagram of the electronic circuitry of an exemplary device.

A block diagram of the circuitry 132 is illustrated in FIG. 2. A battery 22 supplies power to the circuitry. The controller 10 controls the overall operation of the device in accordance with programmed instructions and/or circuit configurations. The controller may be implemented as a microprocessor-based controller and include a microprocessor and memory for data and program storage, implemented with dedicated hardware components such as ASICs (e.g., finite state machines), or implemented as a combination thereof. As the term is used herein, the programming of the controller refers to either code executed by a microprocessor or to specific configurations of hardware components for performing particular functions. A telemetry transceiver 80 is interfaced to the controller which enables the controller to communicate with an external programmer and/or a remote monitoring unit. Sensing circuitry 30 and pacing or pulse generation circuitry 20 are interfaced to the controller by which the controller interprets sensing signals and controls the delivery of pacing pulses in accordance with a pacing mode. The sensing circuitry 30 receives atrial and/or ventricular electrogram signals from sensing electrodes and includes sensing amplifiers, analog-to-digital converters for digitizing sensing signal inputs from the sensing amplifiers, and registers that can be written to for adjusting the gain and threshold values of the sensing amplifiers. The pulse generation circuitry 20 delivers pacing pulses to pacing electrodes disposed in the heart and includes capacitive discharge pulse generators, registers for controlling the pulse generators, and registers for adjusting pacing parameters such as pulse energy (e.g., pulse amplitude and width). The pulse generation circuitry may also include a shocking pulse generator for delivering a defibrillation/cardioversion shock via a shock electrode upon detection of a tachyarrhythmia.

A pacing channel is made up of a pulse generator connected to an electrode, while a sensing channel is made up of a sense amplifier connected to an electrode. Shown in the figure are electrodes $40_1$ through $40_N$ where N is some integer. The electrodes may be on the same or different leads and are electrically connected to a MOS switch matrix 70. The switch matrix 70 is controlled by the controller and is used to switch selected electrodes to the input of a sense amplifier or to the output of a pulse generator in order to configure a sensing or pacing channel, respectively. The device may be equipped with any number of pulse generators, amplifiers, and electrodes that may be combined arbitrarily to form sensing or pacing channels. The switch matrix 70 allows selected ones of the available implanted electrodes to be incorporated into sensing and/or pacing channels in either unipolar or bipolar configurations that may be either atrial or ventricular channels depending upon the location of the electrode.

The device is also equipped with a minute ventilation sensor 25 for measuring the patient's minute ventilation and an activity level sensor 26. The activity level sensor may be any type of motion detector such as an accelerometer inside the pacemaker case that responds to vibrations or accelerations and, after appropriate filtering, produces electrical signals proportional to the patient's level of physical activity. The minute ventilation sensor includes a pair of current source electrodes and a pair of voltage sense electrodes for measuring transthoracic impedance. In rate-adaptive pacing, the pacemaker uses the sensed minute ventilation and/or the accelerometer signal to adjust the rate at which the pacemaker paces the heart in the absence of a faster intrinsic rhythm.

Pacing Modes for Cardiac Resynchronization Therapy

The controller is capable of operating the device in a number of programmed modes where a programmed mode defines the sensing and pacing channels used by the device and how the pacing pulses are output in response to sensed events and expiration of time intervals. Cardiac resynchronization therapy is most conveniently delivered in conjunction with a bradycardia pacing mode. Bradycardia pacing modes refer to pacing algorithms used to pace the atria and/or ventricles in a manner that enforces a certain minimum heart rate. Because of the risk of inducing an arrhythmia with asynchronous pacing, most pacemakers for treating bradycardia are programmed to operate synchronously in a so-called demand mode where sensed cardiac events occurring within a defined interval either trigger or inhibit a pacing pulse. Inhibited demand pacing modes utilize escape intervals to control pacing in accordance with sensed intrinsic activity such that a pacing pulse is delivered to a heart chamber during a cardiac cycle only after expiration of a defined escape interval during which no intrinsic beat by the chamber is detected. In conventional dual-chamber pacing (i.e., pacing pulses delivered to the right atrium and the right ventricle), a ventricular escape interval for pacing the ventricles can be defined between ventricular events, referred to as the cardiac cycle interval (CCI), where the CCI is restarted with a ventricular sense or pace. The inverse of the CCI is the lower rate limit or LRL, which is the lowest rate at which the pacemaker will allow the ventricles to beat. In atrial tracking and AV sequential pacing modes, another ventricular escape interval is defined between atrial and ventricular events, referred to as the atrio-ventricular pacing delay interval or AVD, where a ventricular pacing pulse is delivered upon expiration of the atrio-ventricular pacing delay interval if no ventricular sense occurs before. In an atrial tracking mode or AV sequential mode, the atrio-ventricular pacing delay interval is triggered by an atrial sense or pace, respectively, and stopped by a ventricular sense or pace. Atrial tracking and AV sequential pacing are commonly combined so that an AVD starts with either an atrial pace or sense. An atrial escape interval can also be defined for pacing the atria, either alone or in addition to pacing the ventricles, as an escape interval started by a ventricular sense or pace and stopped by an atrial sense or pace.

As described above, cardiac resynchronization therapy is pacing stimulation applied to one or more heart chambers in a manner that compensates for conduction delays. Cardiac resynchronization therapy is most commonly applied in the treatment of patients with heart failure due to left ventricular dysfunction which is either caused by or contributed to by left ventricular conduction abnormalities. In such patients, the left ventricle or parts of the left ventricle contract later than normal during systole which thereby impairs pumping efficiency. This can occur during intrinsic beats and during paced beats when only the right ventricle is paced. In order to resynchronize ventricular contractions in such patients, pacing therapy is applied such that a portion of the left ventricle is pre-excited by a pace relative to when it would become depolarized during an intrinsic or right ventricle-only paced beat. Optimal pre-excitation of the left ventricle in a particular patient may be obtained with biventricular pacing, where pacing pulses are delivered to the right and left ventricles separated by a specified negative or positive offset interval, or with left ventricle-only pacing.

Existing devices have been configured to deliver biventricular or left ventricle-only pacing using a bradycardia mode based on right heart events. In these modes, an escape interval for delivering paces to the ventricle is restarted (or stopped in the case of the AVD) by a right ventricular pace or sense. A right ventricular sense thus inhibits ventricular pacing, and expiration of the escape interval results in a right ventricular pace, with left ventricular pacing scheduled to occur before or after the expiration. In the case of left-ventricle-only pacing, expiration of the escape interval is marked by a right ventricular pseudo-pace acting as a fiducial point.

CRT has been conventionally delivered as left ventricle-only or biventricular pacing where the left ventricle is paced at a single pacing site, referred to herein as single-site LV pacing. Certain patients may benefit, however, from CRT that delivers paces to multiple left ventricular sites, referred to herein as multi-site LV pacing. Although it is straightforward to transfer certain device behaviors from single-site LV pacing to multi-site LV pacing, others require modification for optimum performance. As discussed below, these device behaviors relate to the management of sensing channel refractory periods, operation of the left ventricular protective period, left ventricle-only pacing in conjunction with right ventricular safety pacing, and switching between LV-only and biventricular triggered pacing.

Refractory Periods for Multi-Site Left Ventricular Pacing

A refractory period for a pacemaker sensing channel refers to a period of time during which the sensing channel is either blind to incoming electrical signals, termed a blanking interval, and/or during which the device is configured to ignore such signals for purposes of sense event detection. It is conventional to blank sensing amplifiers for an interval of time following delivery of a pacing pulse to prevent their saturation. Sensing channels are also rendered refractory after certain pace and sense events in order avoid sensing electrode afterpotentials and preventing cross-talk between the different sensing channels. Refractory periods also often include a retriggerable noise window, where the noise interval usually constitutes the last part of the refractory period. Sensed events occurring within the noise interval will restart the noise interval, thus increasing the length of the refractory period.

Existing devices configured to deliver single-site LV pacing may utilize a right atrial sensing channel, a right ventricular sensing channel, and a left ventricular sensing channel. Refractory periods for the sensing channels in these devices are managed as follows: 1) a sense occurring in a particular sensing channel initiates a refractory period of specified duration for that particular sensing channel, 2) a right atrial refractory period of specified duration is initiated by a right atrial pace, 3) a right atrial refractory period of specified duration is initiated by a left ventricular or right ventricular pace, 4) a left ventricular refractory period of specified duration is initiated by a right or left ventricular pace, and 5) a right ventricular refractory period of specified duration is initiated by a right or left ventricular pace. Although this scheme is adequate for single-site LV pacing, modifications are necessary for optimal performance in multi-site LV pacing.

FIGS. 3-6 illustrate the disclosed scheme for refractory period management in a multi-site LV pacing situation. Each of the figures shows time lines for the right atrial (A) sensing channel, the right ventricular (RV) sensing channel, and the left ventricular (LV) sensing channel for various programmed settings and cardiac cycle types. The shaded blocks along each time line indicate that the sensing channel is refractory, and the dashed-line block along the LV time line indicates a left ventricular protective period (LVPP) as discussed below. As shown in FIGS. 3-6, the behavior for post-sense refractory periods that are initiated by a right atrial sense AS, a right ventricular sense RVS, or a left ventricular sense LVS is that a sense occurring in a particular sensing channel initiates a refractory period of specified duration for that particular sensing channel.

Figure 3:
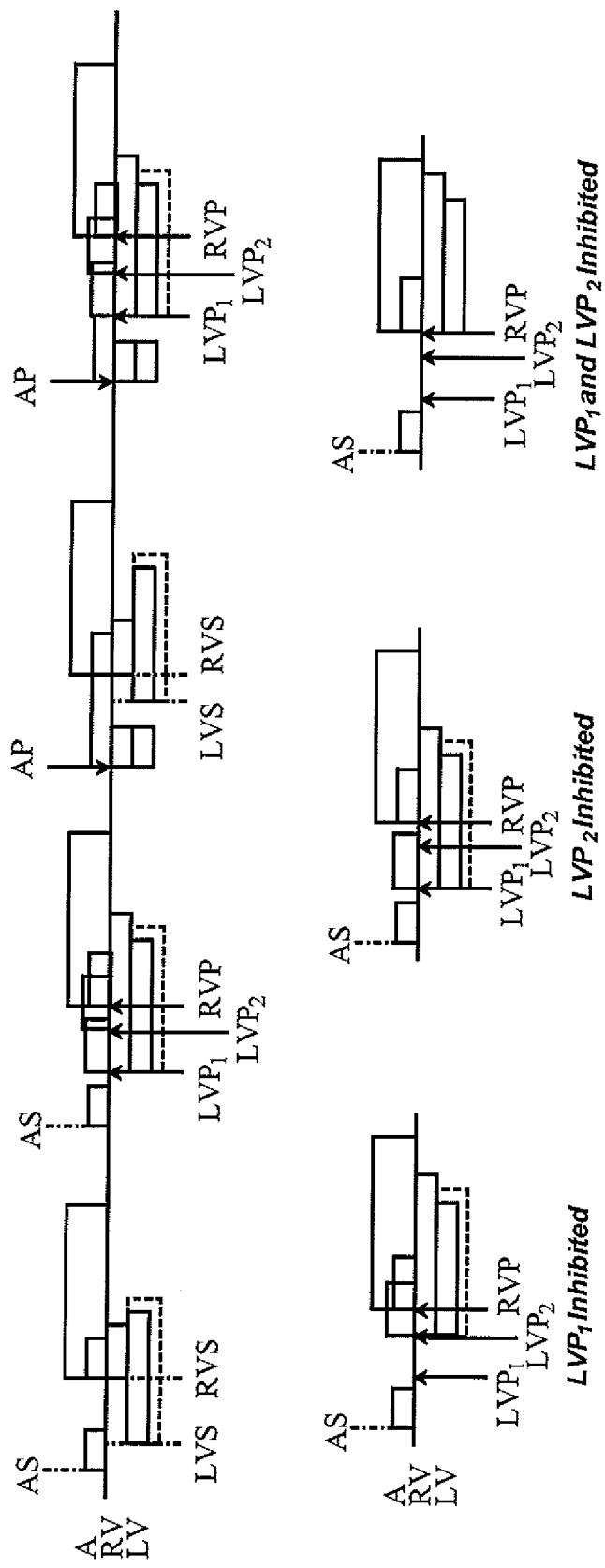
FIGS. 3-6 illustrate the disclosed scheme for refractory period management for multi-site LV pacing.
Figure 4:
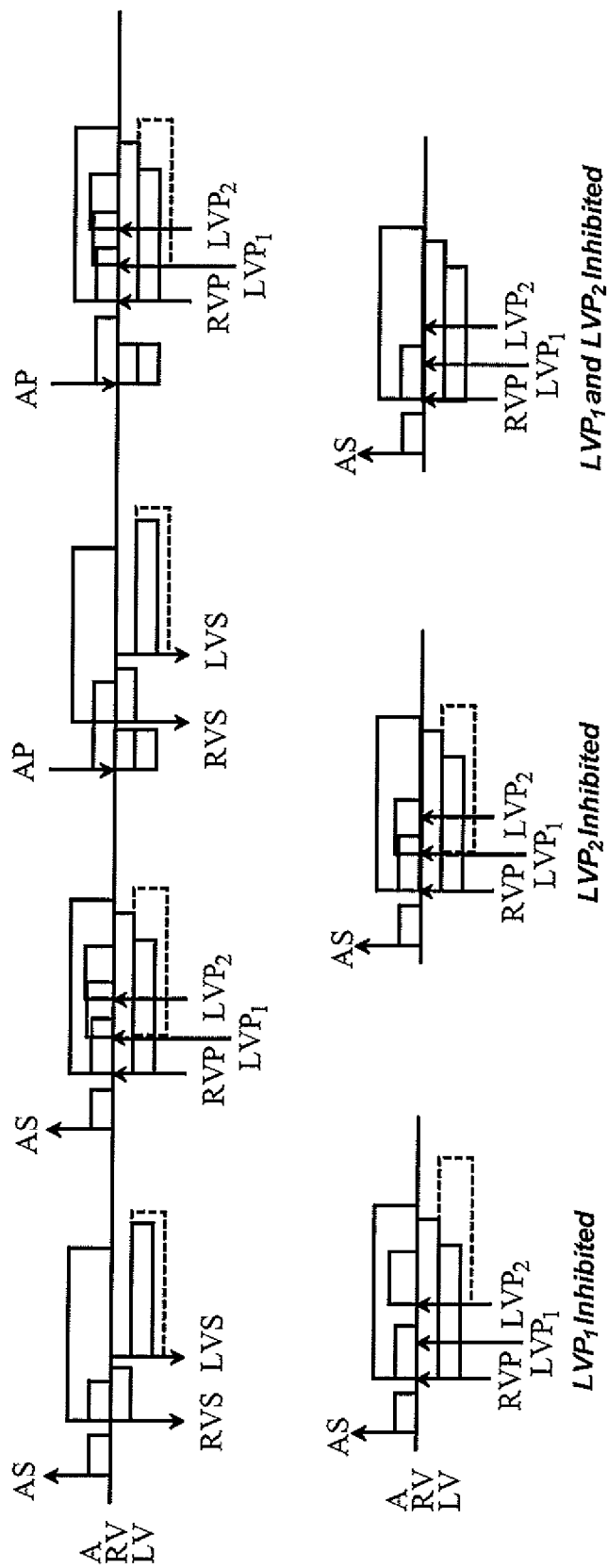
Figure 5:
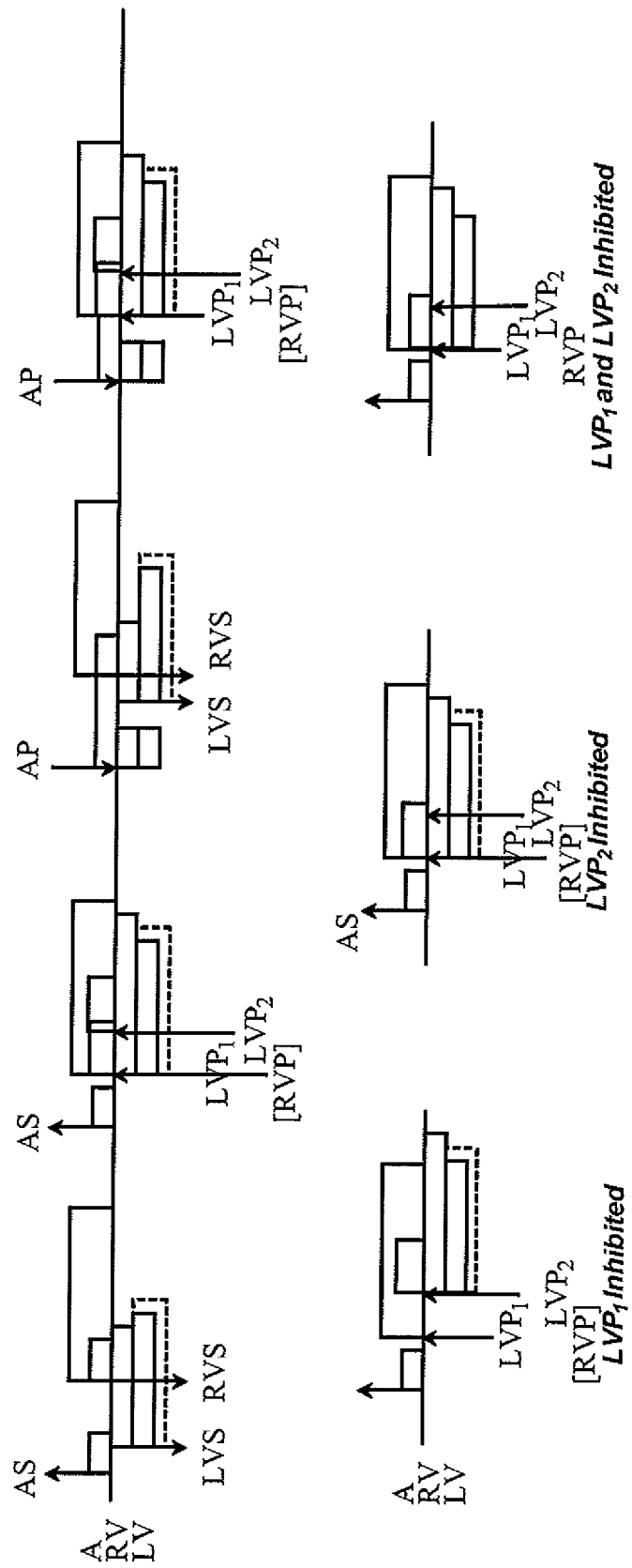
Figure 6:
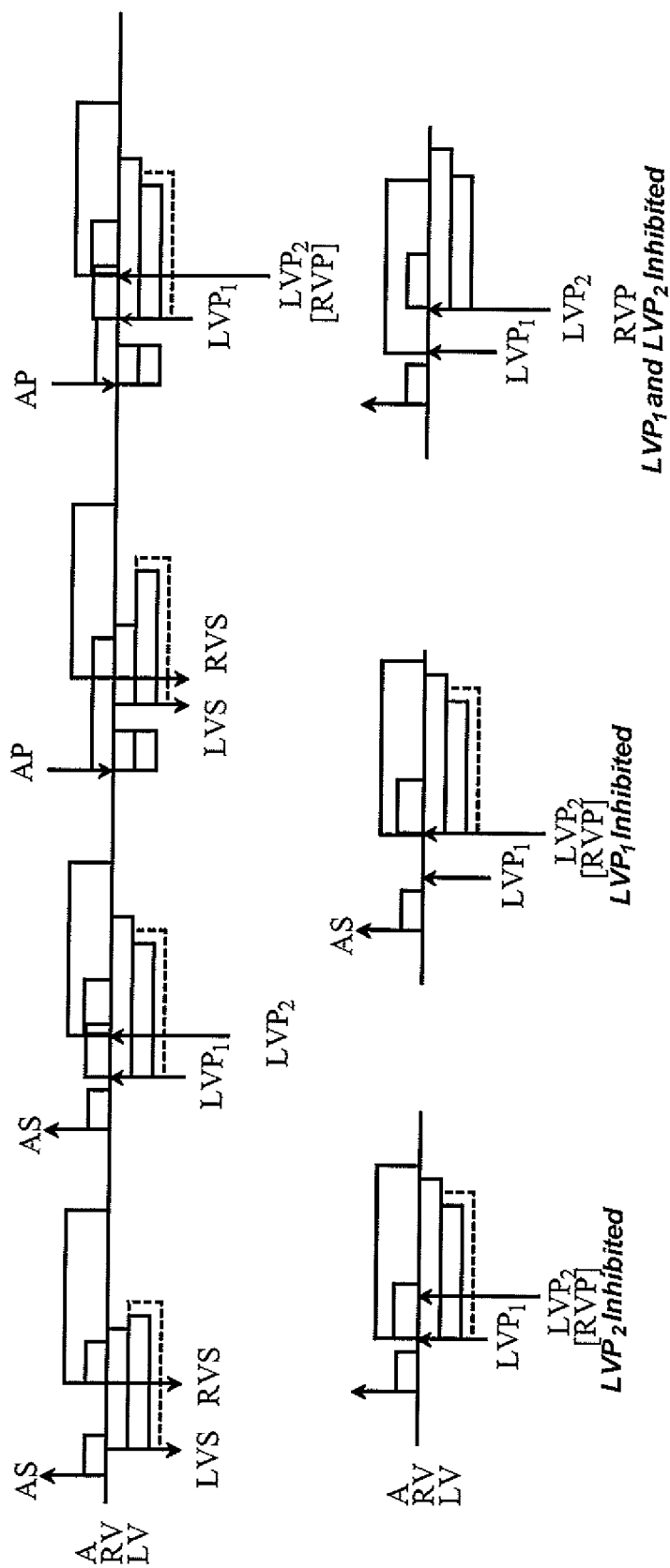

FIG. 3 illustrates the situation for dual-site LV pacing where the LV is paced before the RV, while FIG. 4 illustrates the situation for dual-site LV pacing where the RV is paced first. FIG. 5 illustrates dual-site LV-only pacing where the first left ventricular pace LVP1 to a first LV site is coincident with the right ventricular pseudo-pace [RVP] and the second left ventricular pace LVP2 to a second LV site is delivered afterwards. FIG. 6 illustrates dual-site LV-only pacing where the first left ventricular pace LVP1 occurs before the second left ventricular pace LVP2 coincident with the right ventricular pseudo-pace [RVP]. Note that, in FIG. 3, when RV and LV refractory periods are initiated by a left ventricular pace LVP1, a subsequent left ventricular pace LVP2 and right ventricular pace RVP do not affect those ventricular refractory periods In FIG. 4, when RV and LV refractory periods are initiated by a right ventricular pace RVP, these ventricular refractory periods are unaffected by a subsequent left ventricular pace LVP1 and left ventricular pace LVP2. In both FIGS. 5 and 6, the RV and LV refractory periods initiated by LVP1 are unaffected by LVP2 or the right ventricular pseudo-pace [RVP]. Also, in each situation, the LVP1 and LVP2 paces each triggers an RA refractory period that may use the same settings. Note also that, in all cases, the LVP2 pace does not extend the LVPP initiated by the LVP1 pace.

FIGS. 3-6 show that an RA refractory period is started by a right atrial pace AP. Also, the LVP1 pace starts an RA refractory period, and the subsequent LVP2 pace starts a new RA refractory period. The two RA refractory periods initiated by left ventricular paces preferably share the same settings. Also, if the LVP2 pace falls within the RA refractory period initiated by the LVP1 pace, the RA refractory period initiated by LVP1 terminates. The rationale for this scheme is to restart the RA refractory period after LVP2 for all the same reasons as after LVP1, including restarting the AGC (automatic gain control) and the absolute and retriggerable components of the refractory period. In another embodiment, the LVP2 pace, rather than starting a new RA refractory period, extends the RA refractory period initiated by LVP1 by the LVP1-to-LVP2 interval. Note that this is not the same as starting a new refractory period since the retriggerable components and AGC would be different.

FIGS. 3-6 also show that both the RV and LV post-pace refractory periods start on the first ventricular pace in the pacing sequence that creates a ventricular depolarization.

The post-pace refractory periods for RV and LV are the preferably the same for LVP1 and LVP2. Note that, if one or more LV paces is inhibited (e.g., due to the LVPP), then the RV and LV post-pace refractory periods start for all ventricular sensing channels on the first remaining ventricular pace in the pacing sequence that creates a ventricular depolarization. The refractory behavior depicted in FIGS. 3-6 can also be extended to more than one LV sensing channel and more than two LV pacing sites.

Left Ventricular Protection Period for Multi-Site Left Ventricular Pacing

Figure 7:
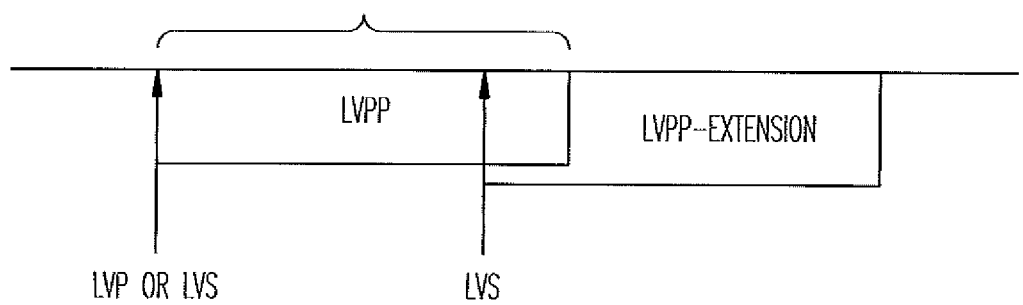
FIGS. 7-10 illustrate implementation of a left ventricular protective period for multi-site LV pacing.

In a pacing mode where the left ventricle is paced upon expiration of an escape interval that is reset by a right ventricular sense, there is the risk that the left ventricular pace may be delivered in the so-called vulnerable period that occurs after a depolarization and trigger an arrhythmia. To reduce this risk, existing devices that deliver single-site LV pacing based on right heart events have implemented a left ventricular protective period (LVPP) that is initiated by a left ventricular sense or pace and during which further left ventricular pacing is inhibited. FIG. 7 depicts the behavior of the LVPP algorithm in existing devices. All LV paces are inhibited during LVPP other than the LV pace that triggers LVPP. Either a non-refractory LV sense or an LV pace initiates LVPP. A non-refractory LV sense during LVPP restarts LVPP and therefore extends the LV pace inhibition period.

Delivery of a multiple LV pacing pulses during a single cardiac cycle requires that the LVPP behavior employed in those existing devices be modified. Without modification, the LV pacing pulses after the first pulse would be inhibited by LVPP, and some additional pacing hazards may be unmitigated. Several options exist for LVPP behavioral modification; any of which will prevent inhibition of LV pacing pulses after the first LV pacing pulse while mitigating the LV pacing hazard associated with LV pacing. As described below, there are advantages and disadvantages to the various options.

Figure 8:
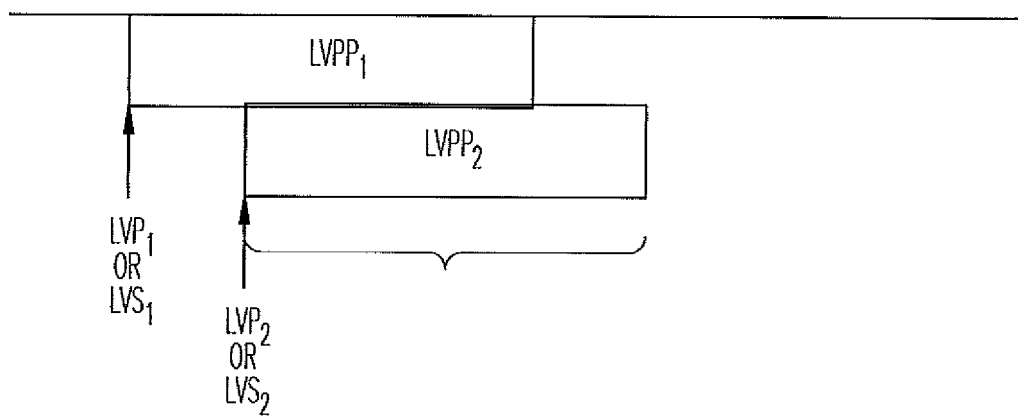

In one option, illustrated for dual-site LV pacing, the existing single LVPP interval is replaced by two LVPP intervals. These two intervals would act independently, the first inhibiting pacing of LV pacing site 1 and the second inhibiting pacing of LV pacing site 2. The behavior of the each LVPP intervals is similar to the existing single LVPP interval. Note that the two LVPP intervals are protecting pacing sites and that these sites could be paced in different sequences in different cardiac cycles. FIG. 8 illustrates this embodiment. As shown, the first LV pace LVP1 is delivered to LV pacing site 1 and initiates left ventricular protective period LVPP1. The second LV pace LVP2 is delivered to LV pacing site 2 and initiates left ventricular protective period LVPP2. The RV pacing pulse may be delivered before LVP1, after LVP2 or in between LVP1 and LVP2. LV paces at the first LV site are inhibited during LVPP1, and LV paces at the second LV site are inhibited during LVPP2. Also as shown in FIG. 8, either a non-refractory LVS or LVP1 initiates LVPP1, and all LV1 paces are inhibited during LVPP1 other than the LVP1 pace that triggered LVPP1. Similarly, either a non-refractory LVS or LVP2 initiates LVPP2, and all LVP2 paces are inhibited during LVPP2 other than the LVP2 pace that triggered LVPP2.

In the particular embodiment illustrated by FIG. 8, two left ventricular sensing channels are used that generate separate sense signals LVS1 and LVS2 from the LVP1 and LVP2 pacing sites, respectively. As depicted, LVS1 and LVS2 may trigger LVPP1 and LVPP2, respectively. Alternatively, the same LVS may be used as a trigger for both LVPP intervals. This option could be used if only a single LV sensing channel is available. Also, a non-refractory LVS retriggers one or both (depending on if one or two LV senses are used) LVPP intervals. This option can be extended to an arbitrary number of LV pacing sites. For example, four LVPP intervals may be used if four LV pacing sites are paced within a single cardiac cycle. An advantage of this option is that each LV site is protected by its own protection period. Another advantage of using multiple LV sense inputs is that it most clearly protects individual LV pacing sites. A disadvantage of multiple LVPP intervals is that the system must manage multiple protection periods within the device and on the user interfaces. A disadvantage of using multiple LV sensing channels is that the system must include additional sensing hardware and manage multiple sensing vectors.

Figure 9:
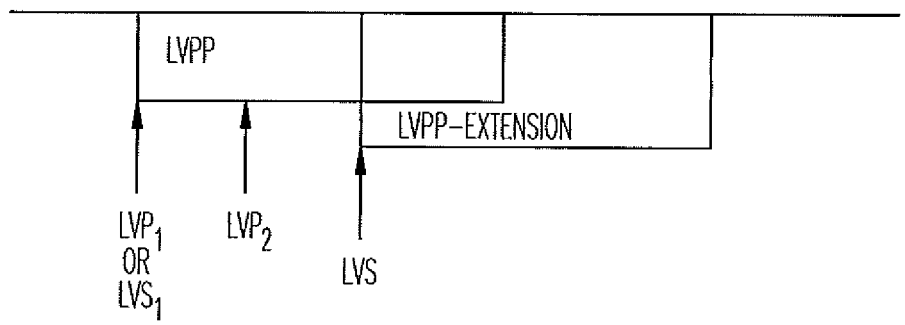

In a second option, a single LVPP interval is used. The LVPP behavior is similar to the existing LVPP behavior except that one LV pacing pulse per LV pacing site is delivered. Specifically, for LVPP intervals triggered by an LV pace, the first LV pace, but only the first pace, per LV pacing site during LVPP is delivered. All other LV paces are inhibited. For LVPP intervals triggered by an LV sense, all LV paces during the LVPP interval are inhibited. The LVPP interval is retriggered by a non-refractory LV sense, but not by LV paces during the LVPP interval (other than the initiating LV pace for LVPP intervals triggered by an LV pace). FIG. 9 illustrates this embodiment. As depicted, either a non-refractory LVS or an LVP to any site initiates LVPP. The LV pace that initiates the LVPP is not inhibited. A non-refractory LV sense during LVPP restarts the LVPP and therefore extends the LV pace inhibition period. The LV pace LVP2 at the second site is not inhibited by the LVPP, and LV paces during the LVPP do not retrigger the LVPP. When using a single LVPP, the LVP1 and LVP2 paces should be closely spaced (e.g. within 100 ms). Given this condition, the rationale for not restarting LVPP on the LVP2 pace is that a subsequent LVP1 will not occur soon enough to fall within an LV vulnerable period of the LVP2 pacing site. Also, in this embodiment, LVP2 is inhibited during an LVPP initiated by LVP1 if a non-refractory LV sense occurs between the delivered LVP1 and the inhibited LVP2. As shown in FIG. 9, a single LV sense LVS may trigger and retrigger LVPP. This option could be used if only a single LV sensing channel is available. Alternatively, LV senses from multiple LV sensing channels may be used as a trigger and retrigger the LVPP interval. The advantage of the single LVPP interval is simplicity; only one interval needs to be managed within the pulse generator and on the user interfaces. This option still provides adequate protection if the LV pace pulse spacing condition noted above is met. The disadvantage of the single LVPP interval is that some level of LV site pacing protection may be lost as compared to the option using multiple protection periods.

Figure 10:
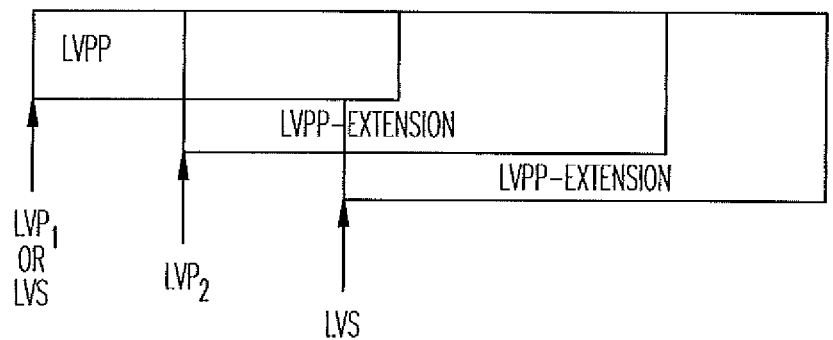

In a third option, a single LVPP interval is also used, but LV paces after the first LV pace retrigger the LVPP interval. This embodiment is depicted in FIG. 10. For LVPP intervals triggered by an LV pace, only the first LV pace per LV pacing site during LVPP is delivered, and all other LV paces are inhibited. For LVPP intervals triggered by an LV sense, all LV paces during the LVPP are inhibited. Either a non-refractory LVS or an LVP to any site initiates the LVPP. A non-refractory LV sense during LVPP restarts LVPP and therefore extends the LV pace inhibition period. The LVP2 pace is not inhibited by the LVPP initiated by LVP1. The second LVP2 restarts the LVPP and therefore extends the LV pace inhibition period. Also as shown in FIG. 10, LV senses LVS from a single LV sensing channel trigger and retrigger the LVPP. This option could be used if only a single LV sensing channel is available. Alternatively, multiple LV sense inputs (e.g. LVS1 and LVS2) from multiple LV sensing channels may trigger and retrigger the LVPP interval. In one embodiment the LVPP extension due to LVP2 is the same as the initial LVPP interval, while in other embodiments it is either shorter or longer than the initial LVPP interval. This option may be required if the LV paces are spaced such that an LVP1 pace may fall within an LV vulnerable period of the LVP2 pacing site.

The LVPP can interfere with high rate LV pacing. To avoid or minimize this problem, the LVPP can be shortened as heart rate increases. If implemented appropriately, this does not place the patient at risk for pacing during the vulnerable time since the QT interval normally shortens (i.e., the vulnerable time moves toward the LV event) with increasing heart rate. This concept (sometimes referred to as LVPP squeeze) is implemented in existing devices and can be extended to operate with any of LVPP schemes for multi-site LV pacing described above.

Another type of protection for the left ventricle implemented in existing single-site LV pacing devices is the ensuring a minimum separation between adjacent pacing LV paces during consecutive cardiac cycles to prevent LV pacing into a vulnerable time. This parameter is the minimum LV pacing interval, designated LVPI. Some physicians may wish to disable LVPP due to, for example, over sensing in the LV causing inappropriate inhibition of LV pacing therapy. If LVPP is disabled a pacing hazard, somewhat hidden from the physician, still needs to be mitigated. The specific hazard arises during, for example, a transition cycle from positive LV offset pacing to negative offset LV pacing where the LV pace is delivered after and before, respectively, the right ventricular pace (or pseudo-pace). Because the next LV pace in the transition cycle occurs sooner than in previous cycles, there is a risk it will occur during the vulnerable period.

Devices capable of multi-site LV pacing may use the same rules for implementing the LVPI as used for implementing the LVPP. Possible exceptions could be that LVPI is triggered only after an LV pace and that LVPI cannot be disabled by the user. Existing systems invoke LVPI on transition cycles where the LV offset changes, and this can also be implemented in multi-site LV systems. However in multi-site LV systems, LVPI may also need to be invoked on transition cycles where: 1) the LV pace to LV pace (e.g. LVP1 to LVP2) interval(s) change, or 2) an additional LV pace is added.

Multi-Site Left Ventricle-Only Pacing and Right Ventricular Safety Pacing

As described above, the LVPP provides protection for the left ventricle when triggered by an LVS. In LV-only pacing, however, if the LVS is due to oversensing, asystole may result. To remedy this, existing devices may employ a right ventricular safety pace that is delivered in place of the right ventricular pseudo-pace when an LVS but no RVS occurs. The basic timing behavior of LV-only pacing in DDD mode in existing devices is that an LV pace is issued at the end of the AV delay unless an RV sense restarts the cardiac cycle interval CCI, LVPP or LVPI inhibits the LV pace, or an LV pace violates the specified minimum CCI interval. If the LV pace is inhibited by LVPP or LVPI, then an RV safety pace is issued instead of the LV pace. If the LV pace would violate the minimum cardiac cycle interval, then the LV pace is delayed to the point where the minimum cardiac cycle interval would not be violated. This scheme is appropriate for single-site LV-only pacing but is inadequate for multi-site LV-only pacing.

In a presently disclosed scheme for multi-site LV-only pacing with right ventricular safety pacing, the LV paces are issued at the end of the AV delay (in e.g., DDD mode) or CCI (in e.g., VVI mode) unless: an RV sense restarts the cardiac cycle interval, LVPP or LVPI inhibits some or all of the LV paces, or one or more of the LV paces violates the minimum CCI. All LV paces that would violate the minimum CCI will be delayed or inhibited All cardiac cycles are defined using only RV events such that an RV pseudo-pace acts as the fiducial for the cardiac cycle when no RV sense occurs. The RV pseudo-pace may, but does not need to, occur coincident with one of the LV paces for cycles where the only ventricular paces are delivered to the left ventricle. An RV safety pace is delivered if all LV paces are inhibited due to LVPP or LVPI and may be issued if some LV paces are inhibited due to LVPP or LVPI.

With regard to the delivery of LV paces, options for implementing the multi-site LV-only pacing scheme as described above include the following (which may be used alone or in combination):
1. Inhibit all LV paces that occur within LVPP or LVPI, deliver any LV paces scheduled for delivery after expiration of LVPP or LVPI at their scheduled times and
    a. Do not pace the inhibited LV sites for current cardiac cycle.
    b. Pace inhibited LV sites immediately after expiration of LVPP or LVPI.
2. If all LV paces before or coincident with the end of the AV delay (in e.g. DDD mode) or CCI (in e.g. VVI mode) are inhibited (due to LVPP or LVPI) but there is at least one LV pace scheduled for delivery after expiration of LVPP or LVPI then
    a. Deliver all LV paces that fall outside LVPP and LVPI at their scheduled times.
    b. Deliver all LV paces that fall outside LVPP and LVPI immediately after expiration of LVPP or LVPI.
    c. Deliver LV paces scheduled inside LVPP and LVPI, immediately after expiration of LVPP or LVPI and all remaining LV paces at their scheduled times.
    d. Deliver all LV paces, including those scheduled inside LVPP and LVPI, immediately after expiration of LVPP or LVPI.
    e. Deliver all LV paces, including those fall inside LVPP and LVPI, immediately after expiration of LVPP or LVPI.
    f. Inhibit all remaining LV paces even though they fall outside LVPP or LVPI.
3. If all LV paces before or coincident with the end of the AV delay (in e.g. DDD mode) or CCI (in e.g. VVI mode) are not inhibited but LV paces after the end of the AV delay or CCI are inhibited then do not issue an RV safety pace.

In the pacing schemes described herein, all cardiac cycles are defined using only RV events. In one embodiment, an RV pseudo-pace acting as the fiducial for the cardiac cycle occur coincident with one of the LV paces for cycles where the only ventricular paces are delivered to the left ventricle. Additional behavior options (not mutually exclusive) for this embodiment include:
1) Align the RV pseudo pace with the end of the AV delay (e.g., in DDD mode) or CCI (e.g., in VVI mode) and one of the LV paces and
    a. Allow additional LV paces only before or coincident with the RV pseudo pace.
    b. Allow additional LV paces only after or coincident with the RV pseudo pace.
    c. Allow additional LV paces before, after or coincident with the RV pseudo pace.
2) Align the RV pseudo-pace with the end of the AV delay (e.g., in DDD mode) or CCI (e.g., in VVI mode) but not one of the LV paces.

Options 1a and 1b above may simplify the user interface and possibly the user's understanding of the system's behavior.

As noted above, in the presently disclosed scheme, an RV safety pace is delivered if all LV paces are inhibited due to LVPP or LVPI and may be issued if some LV paces are inhibited due to LVPP or LVPI. (It should also be noted LV pacing can be inhibited by noise, and this rule may apply to noise inhibited LV paces as well as LVPP or LVPI inhibited paces.) A complicating factor in multi-site LV pacing is that one or more of the leading LV paces may be inhibited but one or more of the lagging LV paces may not be inhibited. (For example, the LVPP may expire during the LV pacing sequence). Another complicating factor is that the LV pace coincident with the RV pseudo-pace may be inhibited while later scheduled LV paces are not inhibited. Therefore to ensure that the AV delay and CCI rules are met, RV safety pacing may be required even if one or LV paces fall outside of the LVPP or LVPI intervals. Options for implementing the multi-site LV-only pacing scheme as just described include the following (which may be used alone or in combination):
1) If all the LV paces are inhibited (due to LVPP or LVPI) then deliver an RV safety pace coincident with the RV pseudo-pace.
2) If one or more LV paces are inhibited (due to LVPP or LVPI) but there is at least one LV pace scheduled for delivery after expiration of LVPP or LVPI, then deliver all LV paces that fall outside LVPP and LVPI at their scheduled times and
    a. Do not deliver an RV safety pace regardless of which LV paces were inhibited.
    b. If all LV paces before and coincident with the RV pseudo-pace are inhibited then
        i. Deliver an RV safety pace coincident with the RV pseudo-pace and inhibit all remaining LV paces even though they fall outside LVPP or LVPI.
        ii. Deliver the RV safety pace coincident with the RV pseudo-pace and deliver all remaining LV paces that fall outside LVPP and LVPI at their scheduled times.
        iii. Deliver the RV safety pace coincident with the RV pseudo-pace and deliver all remaining LV paces immediately after expiration of LVPP or LVPI.
3) If only LV paces after the RV pseudo-pace are inhibited, then do not issue an RV safety pace. (Note: This cannot happen if LV pace refractory time, triggered by the first LV pace, is longer than the duration of the LV pacing sequence)

Biventricular-Triggered Mode for Multi-Site Left Ventricular Pacing

Figure 11:
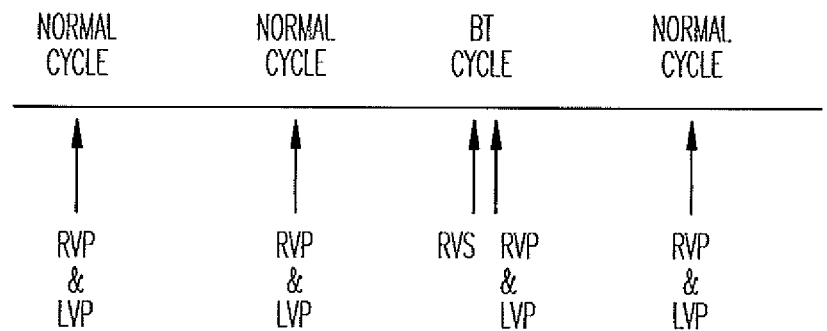
FIGS. 11-15 illustrate implementation of a biventricular-triggered pacing mode for multi-site LV pacing.

In order to optimally resynchronize the ventricles during normal delivery of CRT, the ventricles are paced before intrinsic activation occurs at either of the ventricular pacing sites. However, in some cases intrinsic activation occurs before the scheduled time for pacing pulse delivery. These "escape beats" can occur, for example, during atrial arrhythmias due to the irregular atrial rate or at elevated heart rates due to decreased PR intervals. To at least partially resynchronize the ventricles during these escape beats, existing devices have implemented a biventricular-triggered pacing mode that is switched to when conditions such as mentioned above occur. In this mode, paces are delivered to both the right and left ventricular pacing sites if intrinsic activity is detected at the right ventricular pacing site (i.e. an RV sense occurs). The premise of the algorithm is that, although depolarization has occurred at the right ventricular site, the left ventricular site can still be at least somewhat synchronized by pacing it immediately after the RV sense. Since the RV sense may actually be caused by detection of an LV far field event (in which case it is the RV that needs to be paced), both the RV and LV are paced upon occurrence of an RV sense. Biventricular-triggered pacing, as implemented in existing devices, does not accommodate multi-site LV pacing. This is depicted in FIG. 11. During normal cycles the RV and LV are paced before intrinsic activation occurs at either pacing site. During a biventricular-triggered or BT cycle, both right and left ventricular pacing pulses are delivered immediately after the RV sense.

Figure 12:
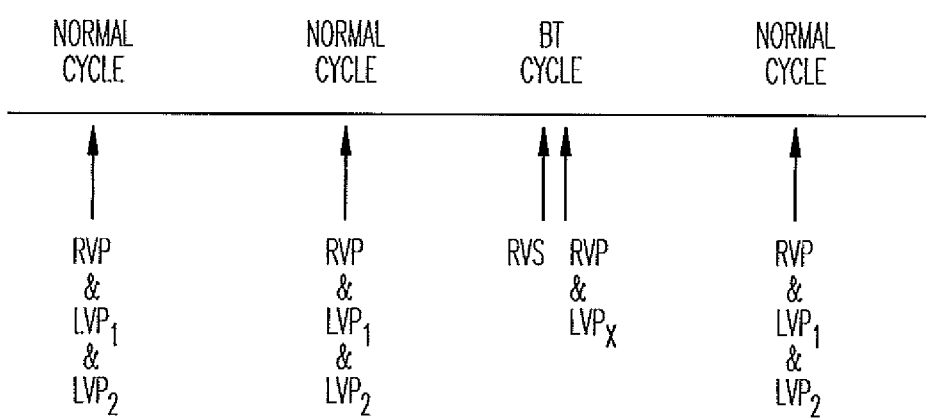
Figure 13:
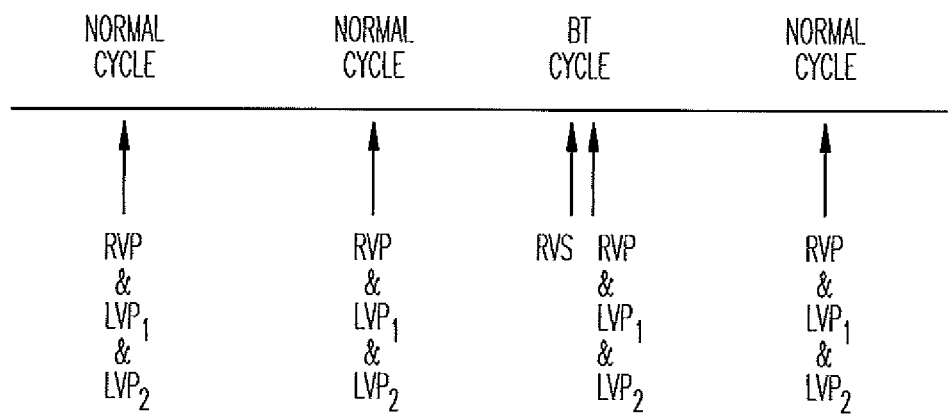
Figure 14:
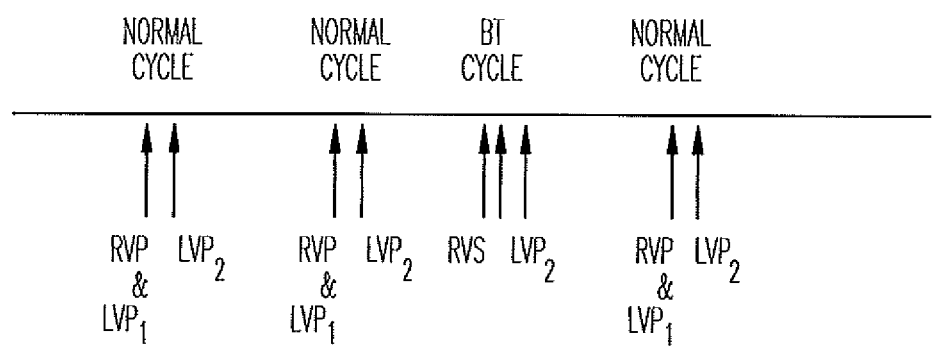
Figure 15:
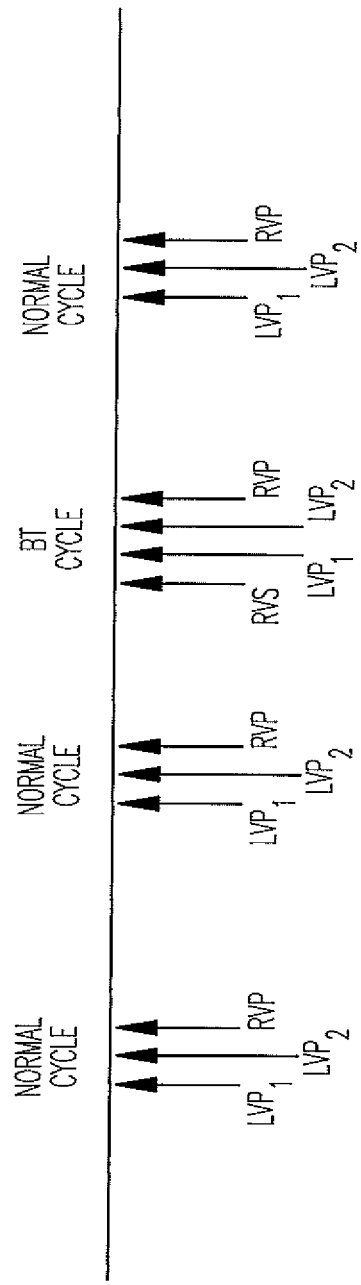

Different embodiments for implementing a biventricular-triggered pacing mode in a multi-site LV pacing situation are illustrated by FIGS. 12-15. For all the embodiments, during normal cycles the RV and multiple LV sites are paced before intrinsic activation occurs at any pacing site. A first embodiment is illustrated by FIG. 12 where, during a BT cycle, the RV and only one of the multiple LV sites are paced immediately after an RV sense. The single LV site is selected from the multiple LV sites to deliver the best resynchronization therapy. The LV site paced during BT therapy may be selected from the LV sites enabled for pace delivery on normal cycle or selected from an LV site that is not enabled for pace delivery in a normal cycle. A second embodiment is illustrated by FIG. 13 where, during a BT cycle, the RV and two or more of the multiple LV sites are paced immediately after an RV sense. The LV sites paced during BT therapy may be selected from the LV sites enabled for pace delivery on normal cycle, may be selected from LV sites that are not enabled for pace delivery in a normal cycle, or may selected from a combination of LV sites enabled and of LV sites not enabled for pace delivery in a normal cycle. A third embodiment is illustrated by FIG. 14 where, during a BT cycle, the RV and one or more of the multiple LV sites are paced immediately after an RV sense. In this embodiment, at least one of the LV sites is paced after the first LV pace(s), and the RV pace occurs simultaneous with or before any LV pace. (It should be appreciated that "simultaneous" in this context means approximately or physiologically simultaneous. Multiple paces delivered at exactly the same time may result in undesirable electrical current paths that can alter pacing thresholds and electrode charge balance. To avoid this effect, paces can be delivered with a small offset (5 ms) and still provide physiologically simultaneous stimulation.) The LV paces sites and/or LV-to-LV interval(s) in the BT cycle may be the same or different as those used in the normal cycle. A fourth embodiment is illustrated by FIG. 15 where, during a BT cycle. the RV and one or more of the multiple LV sites are paced immediately after an RV sense. In this embodiment, at least one of the LV sites is paced after the first LV pace(s), and the RV pace occurs after at least one of the LV paces.

Exemplary Embodiments

In the exemplary embodiments described below, a cardiac pacing device includes pulse generation circuitry for generating pacing pulses, sensing circuitry for sensing cardiac electrical activity, a controller for detecting cardiac events that define pacing timing intervals and for controlling the delivery of pacing pulses in accordance with a programmed mode, and a switch matrix operable by the controller for connecting the pulse generation circuitry and sensing circuitry to selected electrodes in order to form selected sensing and pacing channels. The controller is then programmed to form the appropriate pacing and sensing channels and deliver multi-site LV pacing using the different schemes described herein.

In an exemplary embodiment for implementing refractory periods, where a refractory period is either when a sensing channel is disabled or when sensed activity is ignored for purposes of cardiac event detection, the controller is programmed to sense cardiac activity through a right ventricular sensing channel, schedule delivery of paces through left ventricular pacing channels to at least two left ventricular sites designated LV1 and LV2 during a cardiac cycle interval that is reset by a right ventricular sense, and initiate a post-pace refractory period for the right ventricular sensing channel when the first ventricular pace is delivered during a cardiac cycle. The controller may further be programmed to: 1) sense cardiac activity through a left ventricular sensing channel and initiate a post-pace refractory period for the left ventricular sensing channel when the first ventricular pace is delivered during a cardiac cycle; 2) initiate a post-sense refractory period for any sensing channel when a sense is detected in that sensing channel; 3) sense atrial activity through an atrial sensing channel and initiate a post-pace refractory period for the atrial sensing channel for each ventricular pace delivered during a cardiac cycle; 4) initiate the post-pace refractory periods upon delivering the left ventricular paces to sites LV1 and LV2 use the same programmed settings; 5) deliver a pace to the right ventricle through a right ventricular pacing channel during a cardiac cycle interval and subsequently deliver left ventricular paces to sites LV1 and LV2 during the cardiac cycle interval unless inhibited by a right ventricular sense, reset the cardiac cycle interval upon either a right ventricular sense or a right ventricular pace, after initiation of post-pace refractory periods for the right and left ventricular sensing channels when the right ventricular pace is delivered, leave the post-pace refractory periods unaffected by the subsequent paces to LV1 and LV2; 6) after delivery of delivery of left ventricular paces to sites LV1 and LV2, deliver a pace to the right ventricle through a right ventricular pacing channel during a cardiac cycle interval unless inhibited by a right ventricular sense, reset the cardiac cycle interval upon either a right ventricular sense or a right ventricular pace, after initiation of post-pace refractory periods for the right and left ventricular sensing channels when a first ventricular pace is delivered to site LV1, leave the post-pace refractory periods unaffected by the subsequent pace to site LV2 and the right ventricular pace; 7) deliver a left ventricular pace to site LV1 coincident with a right ventricular pseudo-pace and subsequently deliver a left ventricular pace to site LV2 during a cardiac cycle interval unless inhibited by a right ventricular sense, reset the cardiac cycle interval upon either a right ventricular sense or a right ventricular pseudo-pace, after initiation of post-pace refractory periods for the right and left ventricular sensing channels when a first ventricular pace is delivered to site LV1, leave the post-pace refractory periods unaffected by the subsequent pace to site LV2; 8) deliver a left ventricular pace to site LV1 and subsequently deliver a left ventricular pace to site LV2 coincident with a right ventricular pseudo-pace during a cardiac cycle interval unless inhibited by a right ventricular sense, reset the cardiac cycle interval upon either a right ventricular sense or a right ventricular pseudo-pace, after initiation of post-pace refractory periods for the right and left ventricular sensing channels when the pace is delivered to site LV1, leave the post-pace refractory periods unaffected by the subsequent pace to site LV2; and/or 9) deliver a left ventricular pace to site LV1 and subsequently deliver a left ventricular pace to site LV2 during a cardiac cycle, initiate a left ventricular protective period upon delivering a pace to site LV1 during which all further pacing of site LV1 is inhibited, wherein the left ventricular protective period is unaffected by a pace to site LV2.

In an exemplary embodiment for implementing the LVPP, the controller is programmed to sense cardiac activity through right ventricular and left ventricular sensing channels, schedule delivery of paces through left ventricular pacing channels to at least two left ventricular sites designated LV1 and LV2 during a cardiac cycle interval that is reset by a right ventricular sense, initiate a left ventricular protective period for site LV1 after a left ventricular pace to site LV1 or after a left ventricular sense during which further paces to site LV1 are inhibited, and initiate a left ventricular protective period for site LV2 after a left ventricular pace to site LV2 or after a left ventricular sense during which further paces to site LV1 are inhibited. The controller may be further programmed to: 1) schedule delivery of paces through left ventricular pacing channels to one or more additional left ventricular sites and initiate a separate left ventricular protective period for each additional site after a pace to that site or a left ventricular sense; 2) sense cardiac activity at sites LV1 and LV2 through separate sensing channels, initiate the left ventricular protective period for site LV1 only after a left ventricular pace to site LV1 or after a left ventricular sense at site LV1, initiate the left ventricular protective period for site LV2 only after a left ventricular pace to site LV2 or after a left ventricular sense at site LV1; 3) schedule delivery of paces through left ventricular pacing channels to one or more additional left ventricular sites and initiate a separate left ventricular protective period for each additional site only after a pace to that site or a left ventricular sense at that site; and/or 4) shorten each of the left ventricular protective periods with increasing heart rate. In another embodiment, the controller is programmed to sense cardiac activity through a right ventricular sensing channel, schedule delivery of paces through left ventricular pacing channels to at least two left ventricular sites during a cardiac cycle interval that is reset by a right ventricular sense, and initiate a pace-initiated left ventricular protective period after a left ventricular pace during which all but the first left ventricular pace delivered to a left ventricular site during a cardiac cycle interval are inhibited. The controller may further be programmed to: 1) sense cardiac activity through a left ventricular sensing channel and initiate a sense-initiated left ventricular protective period after a left ventricular sense during which all paces to the left ventricle are inhibited; 2) define selected refractory periods for sensing channels such that when a sensing channel is refractory either the sensing channel is disabled or sensed activity is ignored for purposes of cardiac event detection, initiate post-pace refractory periods for both the right and left ventricular sensing channels when the first ventricular pace is delivered during a cardiac cycle, restart and extend the left ventricular protective period as a sense-initiated left ventricular protective period if a non-refractory left ventricular sense occurs during a pace-initiated or sense-initiated left ventricular protective period, 3) after a left ventricular pace during a pace-initiated left ventricular protective period, restart and extend the left ventricular protective period as a pace-initiated left ventricular protective period; and/or 4) shorten each of the pace-initiated and sense-initiated left ventricular protective periods with increasing heart rate.

In an exemplary embodiment for implementing multi-site LV-only pacing with RV safety pacing, the controller is programmed to sense cardiac activity through right ventricular and left ventricular sensing channels, schedule delivery of paces through left ventricular pacing channels to at least two left ventricular sites during a cardiac cycle interval that is reset by a right ventricular sense, wherein the left ventricular paces are delivered in time relation to expiration of an escape interval that is reset by a right ventricular sense and wherein the expiration of the escape interval is marked by a right ventricular pseudo-pace acting as a fiducial point, initiate a left ventricular protective period after a left ventricular sense during which one or more left ventricular paces are inhibited, and deliver a right ventricular safety pace coincident with the right ventricular pseudo-pace if all scheduled left ventricular paces are inhibited during a cardiac cycle interval either by a left ventricular protective period or otherwise. The controller may further be programmed to: 1) not to deliver a right ventricular safety pace if one or more scheduled left ventricular paces are inhibited during a cardiac cycle interval either by a left ventricular protective period or otherwise but at least one left ventricular pace is scheduled outside of the left ventricular protective period; 2) deliver no right ventricular safety pace and deliver the left ventricular paces that were inhibited by the left ventricular protective period immediately after its expiration if one or more scheduled left ventricular paces are inhibited during a cardiac cycle interval either by a left ventricular protective period or otherwise but at least one left ventricular pace is scheduled outside of the left ventricular protective period; 3) deliver a right ventricular safety pace coincident with the right ventricular pseudo-pace and inhibit all remaining scheduled left ventricular paces during the cardiac cycle interval if all left ventricular paces scheduled to occur before or coincident with the right ventricular pseudo-pace are inhibited during a cardiac cycle interval either by a left ventricular protective period or otherwise; 4) deliver a right ventricular safety pace coincident with the right ventricular pseudo-pace and deliver all remaining scheduled left ventricular paces that fall outside of a left ventricular protective period and are not otherwise inhibited during the cardiac cycle interval at their scheduled times if all left ventricular paces scheduled to occur before or coincident with the right ventricular pseudo-pace are inhibited during a cardiac cycle interval either by a left ventricular protective period or otherwise; 5) deliver a right ventricular safety pace coincident with the right ventricular pseudo-pace and deliver all remaining scheduled left ventricular paces that fall outside of the left ventricular protective period immediately after its expiration if all left ventricular paces scheduled to occur before or coincident with the right ventricular pseudo-pace are inhibited during a cardiac cycle interval either by a left ventricular protective period or otherwise; 6) deliver no right ventricular safety pace if all left ventricular paces scheduled to occur before or coincident with the right ventricular pseudo-pace are not inhibited during a cardiac cycle interval either by a left ventricular protective period or otherwise; 7) enforce a minimum cardiac cycle interval and inhibit left ventricular paces that would otherwise violate the specified minimum cardiac cycle interval; 8) inhibit left ventricular paces that would otherwise violate a specified minimum cardiac cycle interval and deliver the left ventricular paces that were inhibited immediately after the minimum cardiac cycle interval has lapsed; and/or 9) enforce a minimum cardiac cycle interval by inhibiting left ventricular paces that would otherwise violate the specified minimum cardiac cycle interval and further programmed to deliver one or more left ventricular paces to specified sites and at specified times after the minimum cardiac cycle interval has lapsed, if all left ventricular paces during a cardiac cycle interval are inhibited for violating the specified minimum cardiac cycle interval.

In an exemplary embodiment for implementing biventricular-triggered pacing in a multi-site LV pacing context, the controller is programmed to: sense cardiac activity through a right ventricular sensing channel; operate in a normal pacing mode or a biventricular-triggered pacing mode; in a normal pacing mode, schedule delivery of paces through left ventricular pacing channels to at least two left ventricular sites during a cardiac cycle interval that is reset by a right ventricular sense; and in a biventricular-triggered pacing mode, when triggered by a right ventricular sense, deliver a pace to the right ventricle through a right ventricular pacing channel and deliver a single pace to the left ventricle at a selected left ventricular site. The controller may further be programmed: 1) such that the selected left ventricular site paced in the biventricular-triggered pacing mode is selected from among the left ventricular sites paced in the normal mode, and/or 2) such that the selected left ventricular site paced in the biventricular-triggered pacing mode is different from the left ventricular sites paced in the normal mode. In another embodiment, the controller is programmed to: sense cardiac activity through a right ventricular sensing channel; operate in a normal pacing mode or a biventricular-triggered pacing mode; in a normal pacing mode, schedule delivery of paces through left ventricular pacing channels to at least two left ventricular sites during a cardiac cycle interval that is reset by a right ventricular sense; and in a biventricular-triggered pacing mode, when triggered by a right ventricular sense, deliver a pace to the right ventricle through a right ventricular pacing channel and deliver multiple paces to the left ventricle at selected left ventricular sites. The controller may further be programmed: 1) such that the selected left ventricular sites paced in the biventricular-triggered pacing mode are selected from among the left ventricular sites paced in the normal mode; 2) such that at least one of the selected left ventricular sites paced in the biventricular-triggered pacing mode is different from the left ventricular sites paced in the normal mode; 3) in the biventricular-triggered mode, to deliver at least one first left ventricular pace coincident with the right ventricular pace immediately after a right ventricular sense and then deliver at least one subsequent left ventricular pace after a selected interval; 4) such that the subsequent left ventricular paces are delivered at selected intervals after the first left ventricular pace that are the same as the intervals between left ventricular paces used in the normal mode; and/or 5) such that the subsequent left ventricular paces are delivered at selected intervals after the first left ventricular pace that are the different from the intervals between left ventricular paces used in the normal mode.

The invention has been described in conjunction with the foregoing specific embodiments. It should be appreciated that those embodiments may also be combined in any manner considered to be advantageous. Also, many alternatives, variations, and modifications will be apparent to those of ordinary skill in the art. Other such alternatives, variations, and modifications are intended to fall within the scope of the following appended claims.

What is claimed is:

1. A cardiac pacing device, comprising:
   pulse generation circuitry for generating pacing pulses;
   sensing circuitry for sensing cardiac electrical activity;
   a controller for detecting cardiac events that define pacing timing intervals and for controlling the delivery of pacing pulses in accordance with a programmed mode;
   a switch matrix operable by the controller for connecting the pulse generation circuitry and sensing circuitry to selected electrodes in order to form selected sensing and pacing channels;
   wherein the controller is programmed to:
   sense cardiac activity through right ventricular and left ventricular sensing channels;
   schedule delivery of paces through left ventricular pacing channels to at least two left ventricular sites designated LV1 and LV2 during a cardiac cycle interval that is reset by a right ventricular sense;
   initiate a first left ventricular protective period for site LV1 after a left ventricular pace to site LV1 or after a left ventricular sense during which further paces to site LV1 are inhibited;
   initiate a second left ventricular protective period for site LV2 after a left ventricular pace to site LV2 or after a left ventricular sense during which further paces to site LV2 are inhibited.

2. The device of claim 1 wherein the controller is programmed to schedule delivery of paces through left ventricular pacing channels to one or more additional left ventricular sites and initiate a separate left ventricular protective period for each additional site after a pace to that site or a left ventricular sense.

3. The device of claim 1 wherein the controller is programmed to:
   sense cardiac activity at sites LV1 and LV2 through separate sensing channels;
   initiate the left ventricular protective period for site LV1 only after a left ventricular pace to site LV1 or after a left ventricular sense at site LV1;
   initiate the left ventricular protective period for site LV2 only after a left ventricular pace to site LV2 or after a left ventricular sense at site LV2.

4. The device of claim 1 wherein the controller is programmed to schedule delivery of paces through left ventricular pacing channels to one or more additional left ventricular sites and initiate a separate left ventricular protective period for each additional site only after a pace to that site or a left ventricular sense at that site.

5. The device of claim 1 wherein the controller is programmed to shorten each of the left ventricular protective periods with increasing heart rate.

6. A cardiac pacing device, comprising:
   pulse generation circuitry for generating pacing pulses;
   sensing circuitry for sensing cardiac electrical activity;
   a controller for detecting cardiac events that define pacing timing intervals and for controlling the delivery of pacing pulses in accordance with a programmed mode;
   a switch matrix operable by the controller for connecting the pulse generation circuitry and sensing circuitry to selected electrodes in order to form selected sensing and pacing channels;
   wherein the controller is programmed to:
   sense cardiac activity through a right ventricular sensing channel;
   schedule delivery of paces through left ventricular pacing channels to a plurality of left ventricular pacing sites during a cardiac cycle interval that is reset by a right ventricular sense;
   initiate a separate left ventricular protective period after a left ventricular pace to any of the left ventricular pacing sites, wherein during the left ventricular protective period only the first pace per left ventricular pacing site is delivered with all other left ventricular paces inhibited.

7. The device of claim 6 wherein the controller is further programmed to:
   sense cardiac activity through a left ventricular sensing channel;

initiate a sense-initiated left ventricular protective period after a left ventricular sense during which all paces to the left ventricle are inhibited.

8. The device of claim 7 wherein the controller is further programmed to:
define selected refractory periods for sensing channels such that when a sensing channel is refractory either the sensing channel is disabled or sensed activity is ignored for purposes of cardiac event detection;
initiate post-pace refractory periods for both the right and left ventricular sensing channels when the first ventricular pace is delivered during a cardiac cycle;
if a non-refractory left ventricular sense occurs during a pace-initiated or sense-initiated left ventricular protective period, restart and extend the left ventricular protective period as a sense-initiated left ventricular protective period.

9. The device of claim 6 wherein the controller is further programmed to, after a left ventricular pace during a pace-initiated left ventricular protective period, restart and extend the left ventricular protective period as a pace-initiated left ventricular protective period.

10. The device of claim 7 wherein the controller is programmed to shorten each of the pace-initiated and sense-initiated left ventricular protective periods with increasing heart rate.

* * * * *